(12) United States Patent
Aggerholm et al.

(10) Patent No.: US 8,454,637 B2
(45) Date of Patent: Jun. 4, 2013

(54) SCORING BALLOON WITH OFFSET SCORING ELEMENTS

(75) Inventors: Steen Aggerholm, St. Heddinge (DK); Per Elgaard, Haslev (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/352,925

(22) Filed: Jan. 18, 2012

(65) Prior Publication Data

US 2012/0191111 A1 Jul. 26, 2012

(30) Foreign Application Priority Data

Jan. 20, 2011 (GB) .................................. 1100985.9

(51) Int. Cl.
*A61B 17/22* (2006.01)

(52) U.S. Cl.
USPC ......................................................... 606/159

(58) Field of Classification Search
USPC ...... 606/84, 159, 167, 170, 192–194; 604/22, 604/96.01, 103.03, 103.06–103.08
See application file for complete search history.

(56) References Cited

U.S. PATENT DOCUMENTS

| | | | | | |
|---|---|---|---|---|---|
| 5,196,024 A | * | 3/1993 | Barath | ........................... | 606/159 |
| 5,209,799 A | * | 5/1993 | Vigil | ........................... | 156/156 |
| 5,320,634 A | * | 6/1994 | Vigil et al. | ..................... | 606/159 |
| 5,336,234 A | * | 8/1994 | Vigil et al. | ..................... | 606/159 |
| 5,616,149 A | * | 4/1997 | Barath | ........................... | 606/159 |
| 5,713,913 A | * | 2/1998 | Lary et al. | ..................... | 606/159 |
| 5,718,684 A | * | 2/1998 | Gupta | ....................... | 604/103.07 |
| 5,797,935 A | * | 8/1998 | Barath | ........................... | 606/159 |
| 6,197,013 B1 | * | 3/2001 | Reed et al. | ..................... | 604/509 |
| 6,306,151 B1 | * | 10/2001 | Lary | ............................. | 606/159 |
| 6,562,062 B2 | * | 5/2003 | Jenusaitis et al. | ............. | 623/1.11 |
| 6,632,231 B2 | * | 10/2003 | Radisch, Jr. | .................. | 606/159 |
| 6,730,105 B2 | * | 5/2004 | Shiber | .......................... | 606/159 |
| 6,942,680 B2 | * | 9/2005 | Grayzel et al. | ................ | 606/194 |
| 7,172,609 B2 | | 2/2007 | Radisch, Jr. | | |
| 7,270,673 B2 | * | 9/2007 | Yee et al. | ..................... | 606/159 |
| 7,291,158 B2 | | 11/2007 | Crow et al. | | |
| 7,303,572 B2 | | 12/2007 | Melsheimer et al. | | |
| 7,662,163 B2 | | 2/2010 | Grayzel et al. | | |
| 8,038,691 B2 | * | 10/2011 | Bence et al. | .................. | 606/159 |
| 2002/0010489 A1 | | 1/2002 | Grayzel et al. | | |
| 2003/0040770 A1 | | 2/2003 | Radisch, Jr. | | |
| 2003/0144683 A1 | * | 7/2003 | Sirhan et al. | .................. | 606/194 |
| 2004/0133223 A1 | * | 7/2004 | Weber | ........................... | 606/159 |
| 2004/0133233 A1 | | 7/2004 | Sepetka et al. | | |
| 2005/0038383 A1 | * | 2/2005 | Kelley et al. | ............. | 604/103.06 |
| 2005/0080478 A1 | | 4/2005 | Barongan | | |
| 2005/0137618 A1 | * | 6/2005 | Kunis | ............................. | 606/192 |
| 2005/0288629 A1 | | 12/2005 | Kunis | | |
| 2006/0106413 A1 | * | 5/2006 | Bence et al. | .................. | 606/192 |

(Continued)

*Primary Examiner* — Ryan Severson
(74) *Attorney, Agent, or Firm* — Richard J. Godlewski

(57) ABSTRACT

A scoring balloon (10) includes a balloon portion (12) having a balloon wall substantially even in wall thickness; a plurality of sets of scoring elements (24-28) disposed on the balloon (12); each set of scoring elements including a plurality of scoring elements (30) arranged longitudinally in series, wherein adjacent scoring elements (30) in the series are longitudinally spaced from one another so as to provide gaps (32) between said adjacent scoring elements; each set of scoring elements being radially spaced relative to the other sets of scoring elements around the balloon (12), wherein the scoring elements of one set are longitudinally offset relative to the scoring elements of an or each adjacent set of scoring elements.

15 Claims, 2 Drawing Sheets

U.S. PATENT DOCUMENTS

2006/0135980 A1 6/2006 Trinidad
2006/0178685 A1 8/2006 Melsheimer
2006/0184191 A1 8/2006 O'Brien
2009/0192537 A1 7/2009 O'Brien

* cited by examiner

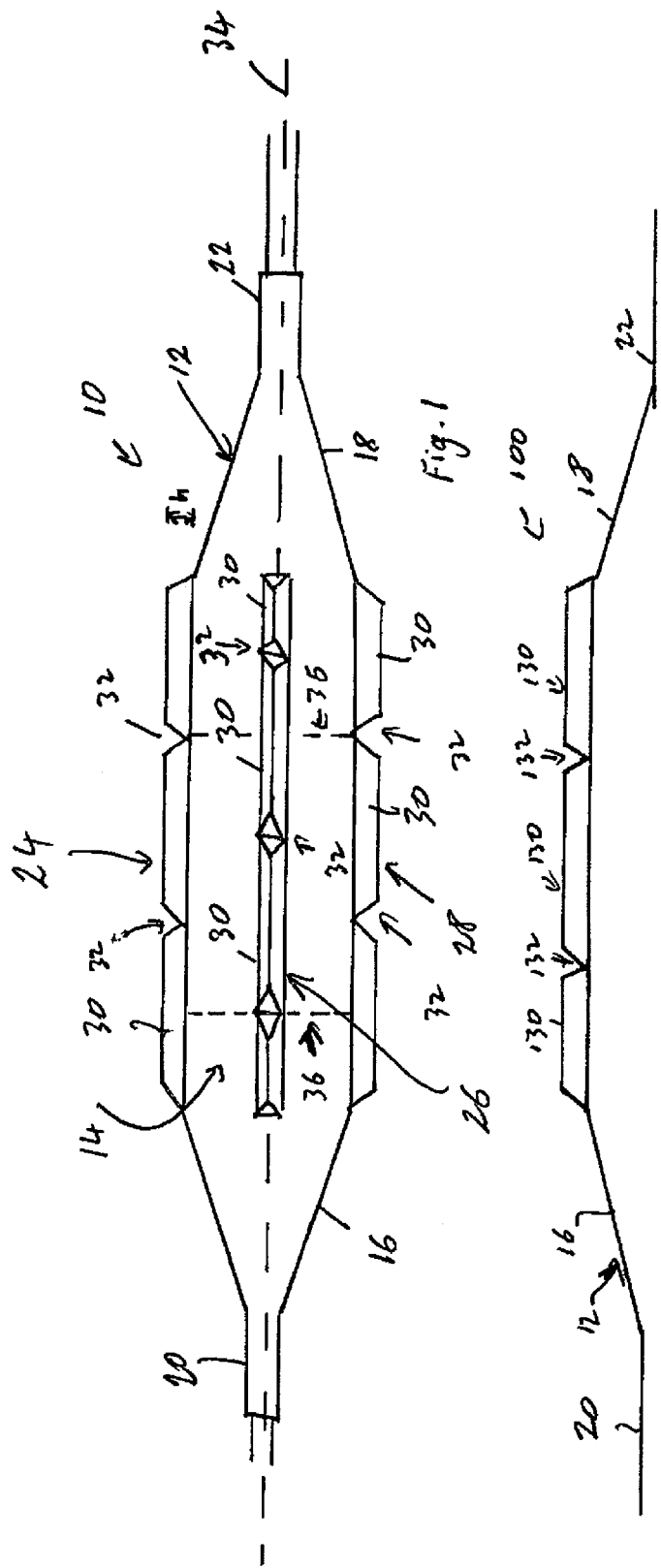

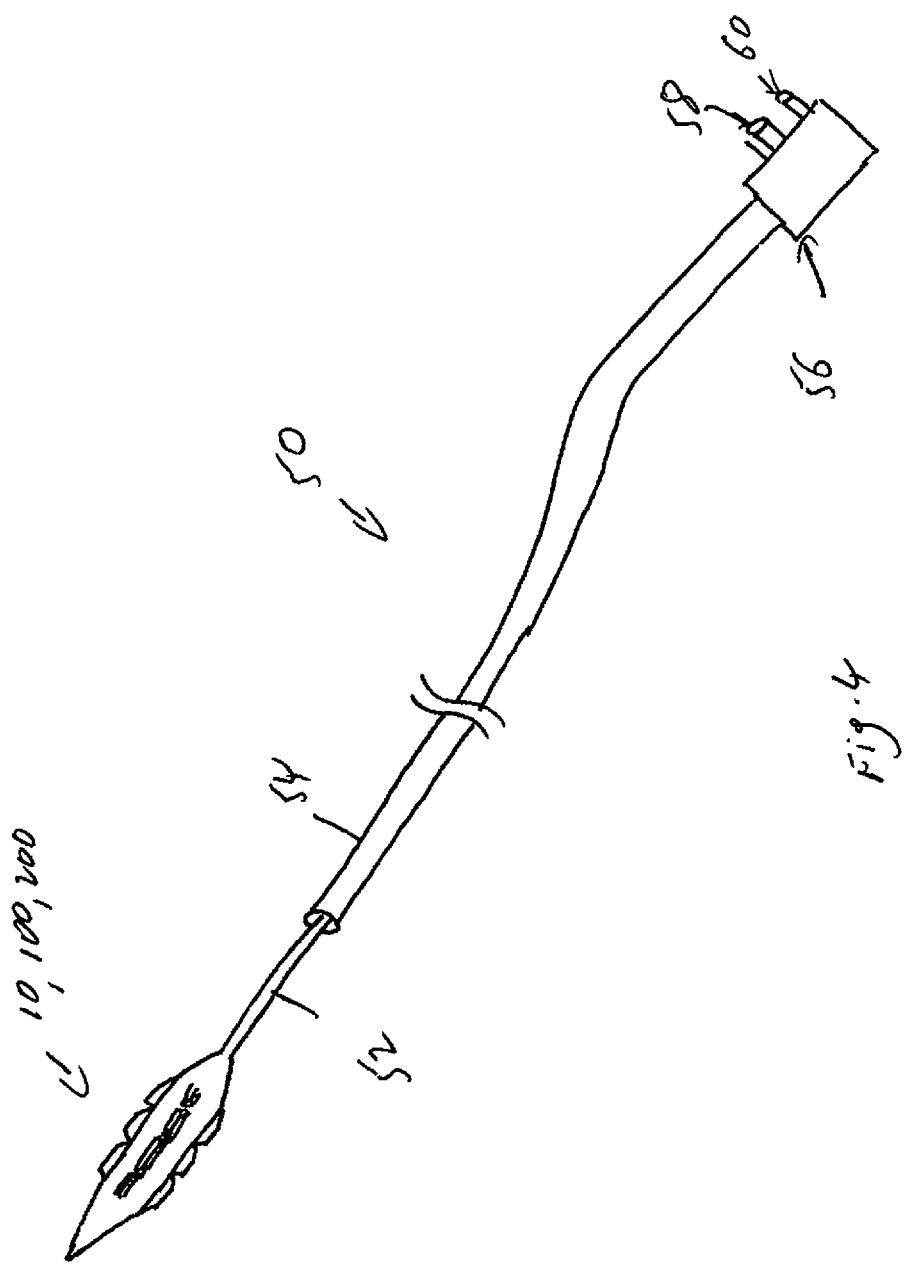

SCORING BALLOON WITH OFFSET SCORING ELEMENTS

TECHNICAL FIELD

The present invention relates to a scoring balloon and to angioplasty treatment apparatus.

BACKGROUND OF THE INVENTION

Scoring or cutting balloons are used in angioplasty procedures to open or dilate vessels constricted by stenosis, fibrous or calcified matter and so on.

These balloons are used to cut into and break off the obstructing material which may then be collected, for instance by a suitable filter device, by aspiration and so on.

There are compromises with the designs of many known cutting balloons, including needing to retain longitudinal flexibility to enable the balloon to pass through tortuous vasculature during its introduction into the patient and to be able to be used in curved parts of a vessel. Often, such balloons also need to be operated at high pressures in order to be able to apply adequate cutting force on the stenotic material. High pressure can lead to increased risk of tearing of the balloon.

Some prior art cutting or scoring balloons are disclosed in U.S. Pat. No. 7,662,163, US-2009/0192537, U.S. Pat. No. 7,172,609, U.S. Pat. No. 7,303,572, U.S. Pat. No. 7,291,158, US-2006/0135980, US-2005/0288629 and US-2006/0178685.

SUMMARY OF THE INVENTION

The present invention seeks to provide an improved scoring balloon and an improved angioplasty treatment apparatus.

According to an aspect of the present invention, there is provided a scoring balloon including a balloon portion having a balloon wall substantially even in wall thickness; a plurality of sets of scoring elements disposed on the balloon; each set of scoring elements including a plurality of scoring elements arranged longitudinally in series, wherein adjacent scoring elements in the series are longitudinally spaced from one another so as to provide gaps between said adjacent scoring elements; each set of scoring elements being radially spaced relative to the other sets of scoring elements around the balloon, wherein the scoring elements of one set are longitudinally offset relative to the scoring elements of an or each adjacent set of scoring elements.

This structure of scoring balloon provides the device with increased flexibility, low slippage characteristics and advantageous tear properties.

Advantageously, the scoring elements are integral with the balloon, preferably being unitary with the balloon. The term unitary as used herein is intended to denote being from one and the same element, for example formed as a co-extrusion or otherwise formed as a single piece.

Preferably, the scoring elements are formed of the same material or materials as the balloon. In other embodiments, they may be made of a different material, for instance a more rigid material but this is not essential.

In a practical embodiment, each set of scoring elements is in the form of a rib provided with one or more notches therein, said notches defining said scoring elements. The notches may extend to the base of the rib or may extend partially through the depth of the rib.

Typically, the scoring elements extend longitudinally along the balloon and are arranged substantially linearly in each set.

It is preferred that the sets of scoring elements are substantially evenly spaced radially around the balloon.

In a practical embodiment, the balloon includes a balloon body portion and first and second end portions, the scoring elements extending along the balloon body portion. The balloon body portion is substantially cylindrical, although in other embodiments may have a non-cylindrical shape.

Advantageously, the scoring elements are substantially all of the same height. In another embodiment, the scoring elements have different heights.

The present invention is also directed to angioplasty treatment apparatus including a scoring balloon as taught herein. The angioplasty treatment apparatus may include other components, such an introducer assembly, an endoluminal filter and so on.

BRIEF DESCRIPTION OF THE DRAWING

Embodiments of the present invention are described below, by way of example only, with reference to the accompanying drawings, in which:

FIG. 1 is a perspective view in schematic form of an embodiment of scoring balloon;

FIG. 2 is a side elevational view of one embodiment of scoring elements;

FIG. 3 is a side elevational view of another embodiment of scoring elements; and FIG. 4 is a side elevational view of one embodiment of scoring elements;

DETAILED DESCRIPTION

Referring to FIG. 1, there is shown an embodiment of scoring balloon. The term scoring is used herein to denote both scoring and cutting.

FIG. 1 is a perspective view of the preferred embodiment of scoring balloon 10, which is formed of a balloon element 12 on which there are provided four sets of scoring elements described in further detail below. The balloon element 12 may be formed of conformable or relatively non-conformable materials such as nylon, preferably nylon 12, Pebax, polyurethane, PET, PE and other similar materials, blends of these, with or without the addition of other functional materials such as radio opaque materials like tungsten, and so on. The balloon element 12 is inflatable and thus impermeable or substantially impermeable, as well as being wrappable to a relatively small diameter for endoluminal delivery.

The balloon element 12 has a body portion 14 which in this example is substantially cylindrical, first and second end cones 16, 18, each bounded by a respective neck portion 20, 22. These elements 14-22 of the balloon element 12 are typically formed by inflation and heating of a raw tubing within a suitable mold. The inflation forms the conical ends 16, 18 as well as the body portion 14.

It is preferred that the balloon element 12 has relatively thin walls. The thickness of the balloon wall typically depends upon the size of the balloon (its diameter) and will typically be in the region of a few micrometers, such as 8 micrometers or so, for a small balloon and in the region of a few tens of micrometers, for example 50 micrometers or so, for a large diameter balloon. In this embodiment, the balloon body portion 14 is formed of a wall which has a uniform wall thickness.

The end cone portions 16, 18 will typically have a wall thickness which increases in the direction of narrowing of the taper, as a result of the lesser amount by which these portions expand during formation of the balloon. However, the end cones may be formed so as to have even wall thicknesses.

Disposed on the outer surface of the balloon element 12 is a plurality of sets of scoring elements, of which only three sets are 24-28 are visible in the Figure, the fourth set being on the non-visible side of the balloon, in this embodiment diametrically opposed to the set 26. Thus, in this embodiment, the sets of scoring elements are disposed in radial positions around the balloon element 12 which are cylindrically spaced from one another by around 90 degrees.

The scoring elements of each set 24-28 preferably extend only along the body portion 14 of the balloon element 12, that is they end at or before the location of the end cones 16, 18. It is not excluded, however, that the scoring elements could extend down the end cones 16, 18, possibly also along the necks 20, 22.

Each set 24-28 of scoring elements includes a plurality of scoring members 30 which are spaced from one another by a gap 32. The scoring members 30, as well as the sets 24-28, are in this embodiment substantially straight and extend substantially linearly along the longitudinal axis 34 of the balloon 10. In other embodiments, they may not be linear although this is not preferred.

In embodiments in which the sets 24-28 of scoring elements extend over substantially the same length along the balloon element 12, it will be apparent that some or each set may have scoring members 30 which are of different lengths, as will be apparent with regard to set 26 in FIG. 1.

The sets 24-28 of scoring elements are also offset longitudinally relative to one another, such that the gaps 32 between scoring elements 30 of one set is not aligned in the longitudinal direction of the balloon 10 with the gaps 32 of the adjacent sets of scoring elements. In other words, considering a circumferential line 36 around the balloon element 12 from a gap 32 will end at the body of a scoring member 30 of the adjacent sets of scoring elements either side of that gap 32. In the preferred embodiment, the gaps 32 between scoring members 30 of one set of scoring elements are arranged such that they are substantially cylindrically aligned with the centre of the scoring members 30 of the adjacent sets. However, in other embodiments, the gaps 32 could be aligned at a different position along the extend of the scoring members 30.

The scoring elements 24-28 are preferably formed as a single piece with the balloon element 12, typically from a co-extrusion of raw tubing. This creates a unitary structure. The scoring elements 24-28 could be made of the same material or materials as the balloon element 12 but in other embodiments could be formed of a different material or materials. Provision of a different material can still allow co-extrusion with the material of the balloon element.

The scoring members 30 preferably have an even height h relative to the surface of the balloon element 12, although it is not excluded that the scoring members 30 could have different heights and also that one or more of the members 30 may have a varying height, for instance to provide what could be described as a sloping surface or a shaped surface.

As will be apparent from the set 26 of scoring elements, these preferably have a pointed, most preferably triangular, form from their base at the balloon element 12 to their apices. This provides a scoring element having a pointed or sharpened tip, useful in scoring or cutting lesion or obstructing material from a vessel wall.

Referring now to FIG. 2, there is shown one embodiment of scoring members 130 and gaps 132. In this embodiment, the scoring elements are separate from one another in that the gaps 132 extend all the way down to the surface of the balloon element 12.

FIG. 3 shows a different embodiment of scoring members 230 and gaps 232. In this embodiment, the gaps 232 extend only part way down to the surface of the balloon element 12, so as to leave a small sliver 234 of rib material between adjacent scoring members 230.

The embodiment of FIG. 2 optimises the flexibility of the balloon 10 while the embodiment of FIG. 3 enhances the strength of the balloon 10, particularly against tearing.

The scoring members 30, 130, 230 are preferably formed from continuous ribs of material which are then cut to form the notches or gaps 32, 132, 232. Cutting could be by laser cutting, ablation, by a knife or by any other suitable method. The advantage of making the scoring members in this manner is the simplicity of manufacture, in that a continuous length of raw tubing, with ribbing extending therealong, can be produced, inflated to form the scoring balloon shape and then cut to form the scoring members 30, 130, 230.

Referring now to FIG. 4, there is shown an example of introducer apparatus 50, which includes a scoring balloon 10, 100, 200 of the type disclosed and contemplated herein. The apparatus 50 is in the form of an introducer which is deployed endoluminally in a patient and includes a catheter 52 on which the scoring balloon 10, 100, 200 is fitted, the combination typically being termed a balloon catheter, a sheath 54 which covers the balloon 10 and catheter 52 during the endoluminal placement of the assembly 50, and an external manipulation and valving unit 56. The unit 56 can be of a conventional form and is therefore not described in detail herein as its components and structure will be readily apparent to the skilled person. Typically, the unit 56 will include one or more ports 58, 60 for the supply or removal of fluid from components of the assembly 50, such as inflation fluid to the scoring balloon 10, 100, 200.

The scoring balloon 10, 100, 200 is typically fitted into the introducer apparatus 50 in a deflated and wrapped condition, in which it has a small diameter. Upon location of the distal end of the assembly 50 at the site to be treated, the sheath 54 is retracted to expose the balloon 10, 100, 200 and then the balloon is inflated to as to adopt the shape shown in the Figures. The balloon is then manipulated so as to score or cut the lesion or stenotic material lining the vessel walls until these are sufficiently opened or dilated, preferably until all of the lesion or stenotic material has been removed. As known in the art, a suitable anti-restenotic agent can be administered to prevent or reduce the chances of restenosis.

Once the vessel has been dilated, the balloon 10, 100, 200 is deflated and removed from within the patient, typically by being withdrawn back into the sheath 54.

The structure and arrangement of the sets 24-28 of scoring elements of the scoring balloon provide a number of functional and clinical advantages. First, the provision of a plurality of scoring members, each with a shoulder at either end, provides a plurality of edges useful both for scoring or cutting but also for preventing migration or movement of the scoring balloon once this has been inflated in the patient's vessel. This advantage may not exist with scoring elements which are unitary along the length of the balloon element or which otherwise do not provide a series of shoulders or edges of this type. This feature is particularly useful when the balloon does not deploy in a fully straight configuration, for instance because the vessel is curved or the build-up on the inside of the vessel is such as to create a non-cylindrical profile of the balloon.

Second, the provision of a plurality of scoring members 30, 130, 230 which are separate or only marginally coupled along the length of the balloon element 12 enhances the flexibility of the scoring balloon 10, enabling this to navigate better through tortuous vessels during its endoluminal placement, as well as to conform better to the inner surfaces of a vessel to be treated, for instance so as to flex around a volume of lesion or stenotic material.

Off-setting the scoring members 30, 130, 230 of different sets strengthens the balloon preventing its kinking between gaps and also assists in stopping the propagation of any tear in the balloon. Tearing of such scoring balloons is known, particularly in light of the pressures to which they are inflated and the existence of sharp fragments of lesion or stenotic material. A longitudinally extending tear presents no immediate risk to the patient because there is no or little risk of loss of balloon material in the patient and the balloon can be relatively easily withdrawn from the patient. On the other hand, a circumferentially extending tear, if not prevented from worsening, can split the balloon in two and present difficulties in removing the distal part as well as involving potentially serious risk to the patient. With the structure of scoring balloon taught herein, any circumferentially extending tear will be stopped by one or more of the scoring members 30, 130, 230. More specifically, in the taught structure, there is no circumferential annulus which is not covered by at least one scoring member. Considering, for example, the lines 36 in FIG. 1, any tear along any one of these lines, which might allow the tear to propagate through the gap 32, will come to an abrupt stop at the next scoring element 30 along that line 36. Therefore, the taught structure will not allow circumferentially extending tears to propagate all the way around the balloon, thereby to keep the balloon in one piece for removal from the patient.

Although the balloon element 12 is shown to have a body portion 14 which is substantially cylindrical, in other embodiments the body portion may be non-cylindrical. It could, for instance, have a waist or bulge, as it could have a frusto-conical shape.

In some embodiments, the scoring members 30, 130, 230 are formed as separate elements which are then attached to a balloon element 12, for instance by bonding, welding, fusing or any other method.

It is to be understood that although the dependent claims are set out in single dependent form, the features of the dependent claims can be combined with one another as if they were in multiply dependent form.

What is claimed is:

1. A scoring balloon including a balloon portion having a balloon wall substantially even in wall thickness; a plurality of sets of scoring elements disposed on the balloon; each set of scoring elements including a plurality of scoring elements arranged longitudinally in series, wherein adjacent scoring elements in the series are longitudinally spaced from one another so as to provide gaps between said adjacent scoring elements; each set of scoring elements being radially spaced relative to the other sets of scoring elements around the balloon, wherein the scoring elements of one set are longitudinally offset relative to the scoring elements of an or each adjacent set of scoring elements and wherein the gaps between adjacent scoring elements are arranged such that they are substantially cylindrically aligned with the center of the scoring elements of an or each adjacent set.

2. A scoring balloon according to claim 1, wherein the scoring elements are integral with the balloon.

3. A scoring balloon according to claim 1, wherein the scoring elements are unitary with the balloon.

4. A scoring balloon according to claim 1, wherein the scoring elements are formed of the same material or materials as the balloon.

5. A scoring balloon according to claim 1, wherein each set of scoring elements is in the form of a rib provided with one or more notches therein, said notches defining said scoring elements; wherein each rib has a base.

6. A scoring balloon according to claim 5, wherein said notches extend to the base of the rib.

7. A scoring balloon according to claim 5, wherein said notches extend partially through the depth of the rib.

8. A scoring balloon according to claim 1, wherein the scoring elements extend longitudinally along the balloon.

9. A scoring balloon according to claim 1, wherein the scoring elements in a set are arranged substantially linearly.

10. A scoring balloon according to claim 1, wherein the sets of scoring elements are substantially evenly spaced radially around the balloon.

11. A scoring balloon according to claim 1, wherein the balloon includes a balloon body portion and first and second end portions, the scoring elements extending along the balloon body portion.

12. A scoring balloon according to claim 11, wherein the balloon body portion is substantially cylindrical.

13. A scoring balloon according to claim 1, wherein the scoring elements are substantially all of the same height.

14. A scoring balloon according to claim 1, wherein the scoring elements have different heights.

15. An angioplasty treatment apparatus including a scoring balloon;

the scoring balloon including a balloon portion having a balloon wall substantially even in wall thickness; a plurality of sets of scoring elements disposed on the balloon; each set of scoring elements including a plurality of scoring elements arranged longitudinally in series, wherein adjacent scoring elements in the series are longitudinally spaced from one another so as to provide gaps between said adjacent scoring elements; each set of scoring elements being radially spaced relative to the other sets of scoring elements around the balloon, wherein the scoring elements of one set are longitudinally offset relative to the scoring elements of an or each adjacent set of scoring elements and wherein the gaps between adjacent scoring elements are arranged such that they are substantially cylindrically aligned with the center of the scoring members of an or each adjacent set.

* * * * *